(12) United States Patent
Moberg

(10) Patent No.: US 6,362,591 B1
(45) Date of Patent: Mar. 26, 2002

(54) METHOD AND APPARATUS FOR DETECTION OF OCCLUSIONS

(75) Inventor: Sheldon Moberg, Granada Hills, CA (US)

(73) Assignee: MiniMed Inc., Sylmar, CA (US)

( * ) Notice: Subject to any disclaimer, the term of this patent is extended or adjusted under 35 U.S.C. 154(b) by 0 days.

(21) Appl. No.: 09/428,411

(22) Filed: Oct. 28, 1999

Related U.S. Application Data

(60) Provisional application No. 60/106,237, filed on Oct. 29, 1998.

(51) Int. Cl.[7] .................... G05B 19/40; F04B 49/00; A61M 31/00
(52) U.S. Cl. .................... 318/685; 604/67; 417/18
(58) Field of Search ................ 318/254, 685, 318/696; 417/12, 18, 20–22, 32, 35, 36, 38, 42, 43, 44.1, 44.2, 45, 53, 63; 604/65, 67; 128/DIG. 12, DIG. 13

(56) References Cited

U.S. PATENT DOCUMENTS

| | | |
|---|---|---|
| 4,444,546 A | 4/1984 | Pazemenas |
| 4,468,221 A | 8/1984 | Mayfield |
| 4,562,751 A | 1/1986 | Nason et al. |
| 4,601,491 A | 7/1986 | Bell, Jr. et al. |
| 4,619,646 A | 10/1986 | Hernandez et al. |
| 4,678,408 A | 7/1987 | Nason et al. |
| 4,685,903 A | 8/1987 | Cable et al. |
| 4,744,790 A | 5/1988 | Jankowski et al. |
| 4,749,109 A | 6/1988 | Kamen |
| 4,952,205 A | 8/1990 | Mauerer et al. |
| 5,080,653 A | 1/1992 | Voss et al. |
| 5,097,122 A | 3/1992 | Colman et al. |
| 5,121,019 A | 6/1992 | Pradler |
| 5,254,096 A | 10/1993 | Rondelet et al. |
| 5,279,556 A * | 1/1994 | Goi et al. .................... 604/67 |
| 5,292,306 A | 3/1994 | Wynkoop et al. |
| D347,894 S | 6/1994 | Hansen et al. |
| 5,389,078 A | 2/1995 | Zalesky et al. |
| 5,505,709 A | 4/1996 | Funderburk et al. |
| 5,522,799 A * | 6/1996 | Furukawa .................... 604/65 |
| 5,545,152 A | 8/1996 | Funderburk et al. |
| 5,549,574 A | 8/1996 | Townsend |
| 5,554,134 A | 9/1996 | Bonnichsen |
| 5,584,667 A * | 12/1996 | Davis .......................... 417/53 |
| 5,599,323 A | 2/1997 | Bonnichsen et al. |
| D380,262 S | 6/1997 | Van Funderburk et al. |
| 5,637,095 A | 6/1997 | Nason et al. |
| 5,647,853 A | 7/1997 | Feldmann et al. |
| 5,722,545 A | 3/1998 | Rinne |
| 5,947,935 A | 9/1999 | Rhinehart et al. |

FOREIGN PATENT DOCUMENTS

| | | |
|---|---|---|
| DE | 2240694 | 8/1972 |
| WO | 9800157 | 10/1998 |

OTHER PUBLICATIONS

PCT Application PCT/US99/25414, Search Report mailed Feb. 2, 2000.

* cited by examiner

Primary Examiner—Khanh Dang
(74) Attorney, Agent, or Firm—Gates & Cooper LLP

(57) ABSTRACT

A method and apparatus for automatically detecting an occlusion or drive system failure in a medication infusion system is provided. The electrical current to an infusion pump is measured and compared against a baseline average current. If the current exceeds a threshold amount, an alarm is triggered. Alternatively, pump motor encoder pulses are measured during a pump cycle. If the number of pulses do not correspond within a normal range, an alarm is triggered. After any alarm is triggered, the pump motor is driven in reverse for an incremental distance in order to relieve the fluid pressure in the system.

17 Claims, 6 Drawing Sheets

METHOD AND APPARATUS FOR DETECTION OF OCCLUSIONS

This application claims priority from provisional patent application No. 60/106,237, filed Oct. 29, 1998 and which is incorporated herein by reference.

BACKGROUND OF THE INVENTION

1. Field of the Invention

This invention relates generally to improvements in infusion pumps such as those used for controlled delivery of medication to a patient. More specifically, this invention relates to improved methods and apparatuses for detecting occlusions in infusion pump systems.

2. Description of the Related Art

Infusion pump devices and systems are relatively well-known in the medical arts, for use in delivering or dispensing a prescribed medication such as insulin to a patient. In one form, such devices comprise a relatively compact pump housing adapted to receive a syringe or reservoir carrying a prescribed medication for administration to the patient through infusion tubing and an associated catheter or infusion set.

The infusion pump includes a small drive motor connected via a suitable transmission assembly for motor-driven advancement of a reservoir piston to administer the medication to the user. Programmable controls can operate the drive motor continuously or at periodic intervals to obtain a closely controlled and accurate delivery of the medication over an extended period of time. Such infusion pumps are utilized to administer insulin and other medications, with exemplary pump constructions being shown and described in U.S. Pat. Nos. 4,562,751; 4,678,408; 4,685,903; 5,080,653 and 5,097,122, which are incorporated by reference herein.

Infusion pumps of the general type described above have provided significant advantages and benefits with respect to accurate delivery of medication or other fluids over an extended period of time. The infusion pump can be designed to be extremely compact as well as water resistant, and may thus be adapted to be carried by the user, for example, by means of a belt clip. As a result, important medication can be delivered to the user with precision and in an automated manner, without significant restriction on the user's mobility or life-style, including in some cases the ability to participate in water sports.

These pumps often incorporate drive systems which use lead screws or other transmission components coupled to motors. The motors can be of the DC, stepper, solenoid or other varieties. These drive systems typically provide an axial displacement of the syringe or reservoir piston thereby dispensing the medication to the user. Powered drive systems are advantageous since they can be electronically controlled to deliver a predetermined amount of medication by means well known in the art.

In the past, medication infusion pumps have included alarm systems designed to detect and indicate pump malfunction and/or nondelivery of the medication to the patient as a result of an occluded delivery line. Such alarm systems have typically used a high pressure limit switch for activating an alarm when the force applied to the reservoir piston plunger reaches a predetermined upper limit indicative of an occluded medication delivery line. In U.S. Pat. No. 4,562,751, the high pressure switch is positioned at one end of a rotatable lead screw, wherein the mechanical reaction force or backlash between the reservoir plunger and the pressure switch is proportional to the pressure applied to the medication as a result of attempted advancement of the reservoir plunger.

In actual practice, however, such high pressure limit switch systems have several disadvantages. For example, the lead screw must move axially some distance to actuate the switch. If the concentration of the medication requires very small (0.5 microliter) dosage increments, then the axial displacement of the reservoir plunger is designed to be very small per increment. Thus, several increments may be required to initiate an alarm when there is an occlusion. This elapse of several increments before an alarm is initiated may represent less medication delivered to the user than is desired. Moreover, there are frictional considerations. The lead screw mechanism of this pump design includes seals, a drive nut, a lead screw/motor coupling, and a bearing. All of these components have frictional properties. In systems where the high pressure switch is placed at the opposite end of the drive train from the reservoir plunger, the friction associated with these components are additive. These properties are known to change over time thereby making a fixed-setting, high pressure switch less effective.

There exists, therefore, a significant need for further improvements in medication infusion pumps, particularly with respect to providing an early warning of an occlusion or other pump drive system failures. The present invention fulfills this need and provides further related advantages.

SUMMARY OF THE PREFERRED EMBODIMENTS

To overcome the limitations in the prior art described above, preferred embodiments disclose a method and system for detecting occlusions or other pump system failures. Power is applied to a pump motor. A first pump motor current value is measured and a determination made whether the first pump motor current value exceeds a second value. If it does exceed the second value, the pump system is rewound at least to the point of reducing the pressure in the system and an alarm indication is given. A calculation is made of a total number of alarm indications, and a determination is made whether the total number of alarm indications exceeds a third value. If it does, a system error message is given.

In an alternative embodiment of the present invention, input power parameters are applied to a pump motor to provide a first pump cycle. A first encoder count is measured during the first pump cycle and a determination is made whether the first encoder count is less than a first value. If it is less than the first value, the fluid pump system is rewound at least to the point of reducing pressure in the system, and an alarm indication is provided. A calculation is made of a total number of alarm indications which is used to determine whether this exceeds a second value. If so, a system error message is provided. To provide system feedback, a determination is made whether the first encoder count is equal to a third value. If it is not equal to the third value, the input power parameters are adjusted to provide a second pump cycle which, in turn, causes a second encoder count of a different value than the first encoder count. The second encoder count will be greater than the first encoder count if the first encoder count was less than the third value. Alternatively, the second encoder count will be smaller than the first encoder count if the first encoder count was greater than the third value.

In still a further embodiment, an input power parameter is provided to a pump motor to provide a pump cycle. An encoder count is measured during the pump cycle. A torque value corresponding to the encoder count and to the input power parameter is determined. Another determination is made whether the torque value is greater than a first value. If so, the fluid pump system is rewound at least to the point of reducing pressure in the fluid pump system. An alarm indication is also provided. A calculation is made of a total number of alarm indications which is used to determine whether this total exceeds a second value. If so, a system error message is provided.

DETAILED DESCRIPTION OF THE PREFERRED EMBODIMENTS

In the following description, reference is made to the accompanying drawings which form a part hereof and which illustrate several embodiments of the present inventions. It is understood that other embodiments may be utilized and structural and operational changes may be made without departing from the scope of the present inventions.

Figure 1:
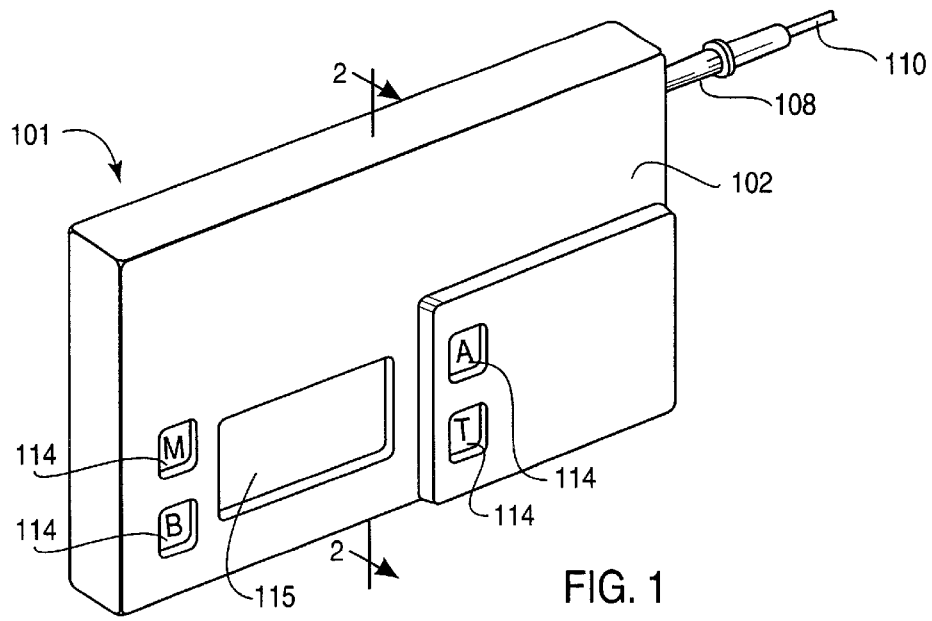
FIG. 1 is a front, perspective view of a medication infusion pump, adapted to include the occlusion detectors claimed herein.

As shown in the exemplary drawings, a medication infusion pump referred to generally in FIG. 1 by the reference numeral 101 is provided for controlled administration of medication to a patient. In accordance with the invention, the infusion pump 101 includes an improved occlusion detector for monitoring and verifying proper delivery of the medication to the patient.

The infusion pump 101 has an overall mechanical construction and mechanical operation which is generally known in the art. More specifically, with respect to FIGS. 1 and 2, the infusion pump 101 comprises a relatively compact pump housing 102 defining an elongated chamber 103 (FIG. 2) for receiving and supporting a syringe 104 charged with a selected medication, such as insulin, to be administered to a patient. The medication-containing syringe 104 includes a syringe barrel 105 joined at the front to a luer neck 106 of reduced diametric size to seat snugly within an outlet port 107 formed in the pump housing 102. A luer fitting 108 is carried on the neck 106 and cooperates with the barrel 105 to fix the syringe in a seated position within the syringe chamber 103. A syringe piston or plunger 109 extends from the aft end of the barrel 105 and may be advanced into the barrel to deliver the medication therefrom. In this regard, the medication is normally dispensed to the patient through a catheter tube 110 adapted for appropriate connection to the luer fitting 108.

The infusion pump 101 includes a compact drive motor 111 (FIG. 2) which is mechanically connected to the syringe plunger 109 for purposes of advancing the plunger in a precision controlled manner to dispense the medication. In this regard, the drive motor 111 is normally powered by a battery power supply 112, in response to operation of a programmable controller 113. As known in the art, the programmable controller 113 can be set by the attending physician, appropriate medical personnel, or the user by an array of buttons 114 on the face or front of the pump housing 102, with a corresponding display panel 115 providing appropriate information regarding set status and/or pump operation. The controller 113 operates the drive motor 111 in a stepwise manner, typically on an intermittent basis, to administer discrete precision doses of the medication to the patient at programmed times.

The mechanical connection between the drive motor 111 and the syringe plunger 109 includes a lead screw assembly 116. More specifically, the drive motor 111 has a rotary output for rotatably driving an elongated lead screw 117 mounted within the pump housing 102. A lead screw nut 118 is carried on the lead screw 117 and includes an appropriate latch arm 119 for engaging a drive flange 120 on the end of the piston plunger 109. Appropriate rotation of the lead screw 117 in response to operation of the motor 111, causes the lead screw nut 118 and associated latch arm 119 to be translated in a precision manner to correspondingly advance the piston plunger 109 and thereby deliver the medication from the syringe barrel 105 and through the catheter tube 110 to the user. Further details regarding the construction and operation of a medication infusion pump of this general type can be found in U.S. Pat. Nos. 4,562,571; 4,678,408; and 4,685,903, which are incorporated by reference herein.

Figure 3:
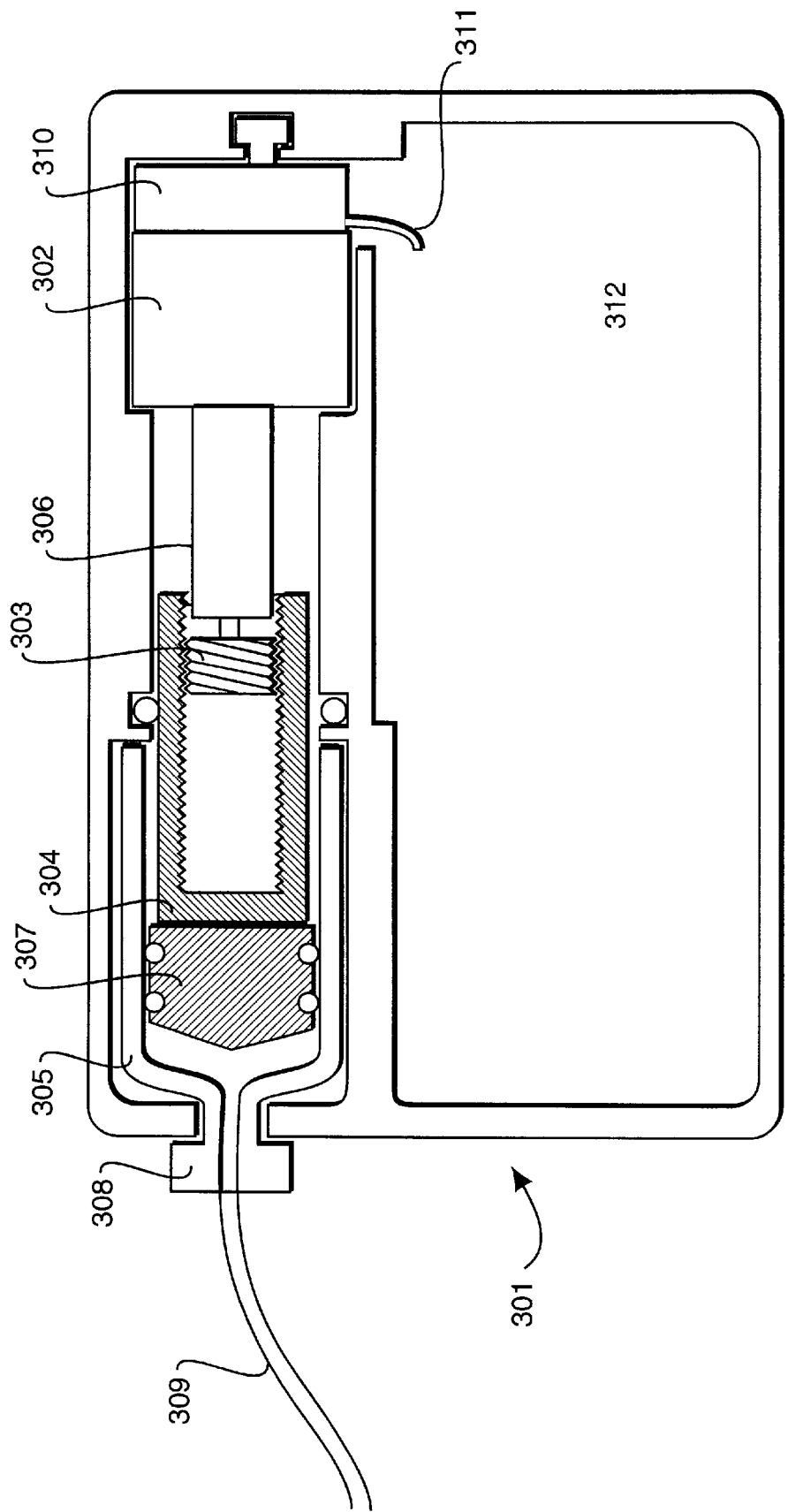
FIG. 3 is a side plan, cut-away view of another infusion pump design, adapted to include the occlusion detectors claimed herein.

FIG. 3 shows another infusion pump design for which an improved occlusion detector may be used. The infusion pump 301 comprises a motor 302, drive screw 303, and plunger slide 304 which are arranged in-line with a reservoir 305. The motor 302 rotates the drive screw 303 via a gear box 306. The drive screw 303 has external threads which engage the internal threads of the plunger slide 304. Thus the rotational torque of the drive screw 303 is translated into axial force of the plunger slide 304. The plunger slide 304 is in contact with a reservoir plunger 307, and advances it thereby forcing the medication out of a luer fitting 308 and into infusion set tubing 309.

Attached to the rear of the motor 302 is an encoder 310, a device known in the art which is capable of counting motor rotations or fractional rotations. The encoder has signal and power supply cables 311 which extend into the battery/electronics compartment 312 of the pump housing. The pump drive mechanism design of FIG. 3 is described in greater detail in copending application Ser. No. 09/429,352, filed contemporaneously which application is incorporated by reference in its entirety.

Figure 4:
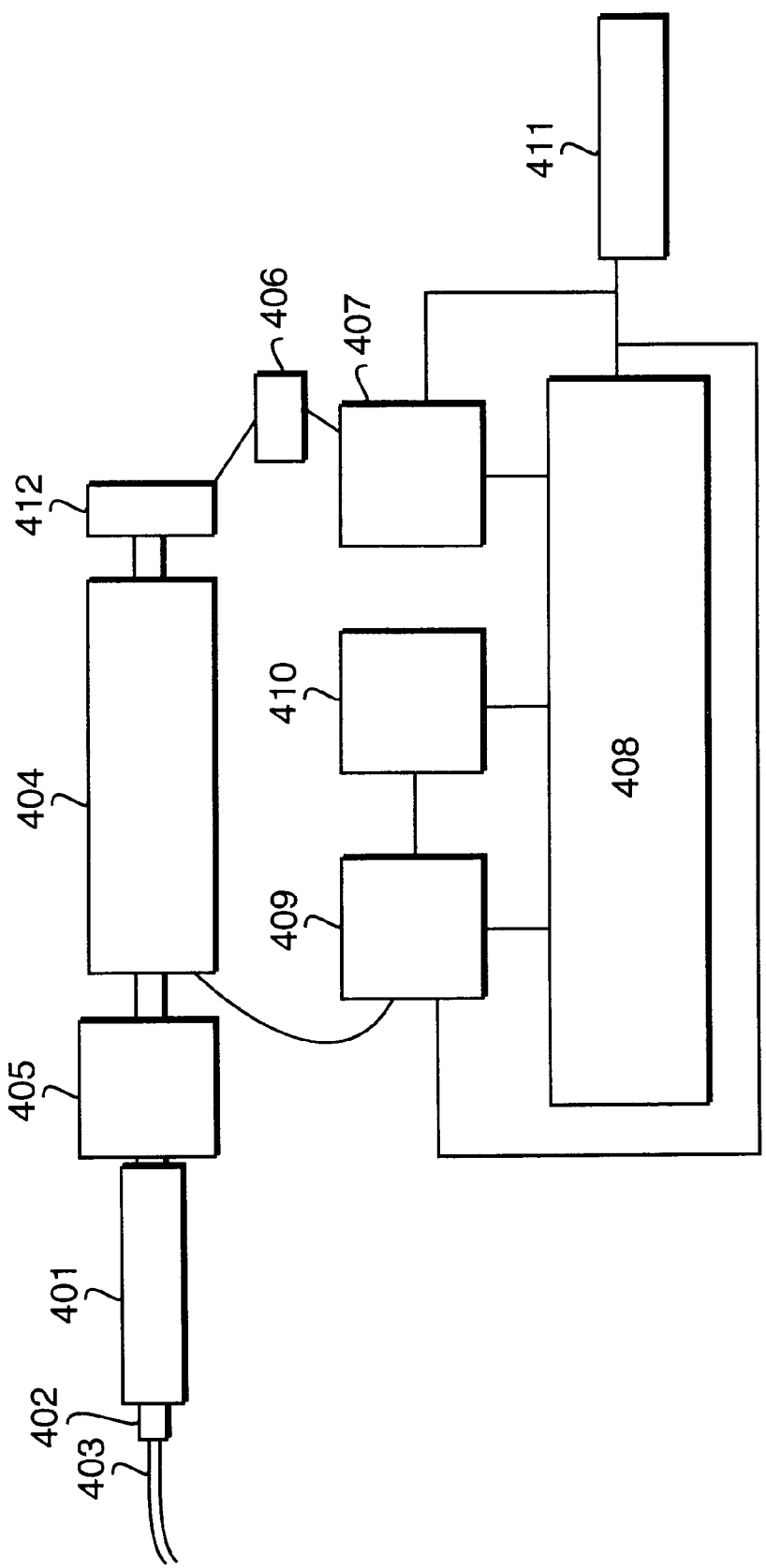
FIG. 4 is a block diagram illustrating a software and hardware environment in which some embodiments of the present invention may be implemented.

FIG. 4 illustrates one software and hardware environment in which certain embodiments of the present invention may be implemented. A syringe or reservoir 401 with a luer fitting 402 and infusion set tubing 403 is connected to a motor drive train. The drive train comprises a motor 404 and a transmission 405 coupling the motor 404 to the reservoir 401. Other reservoir and drive train systems may be used, however, as described herein or as known in the art or as may be developed in the future. At one end of the motor 404 is an encoder system comprised of an encoder wheel 412 and an encoder sensor 406.

The encoder could be magnetic, optical, or other designs known in the art. When the encoder is attached to a motor, it provides a measurement of the rotational displacement of the motor. The accuracy of this measurement is a function of the count resolution of the encoder. If for example, the encoder had a resolution of 360 counts per motor revolution, then with each motor revolution, the sensor will provide 360 encoder signal pulses. If a pump system was designed to require one complete motor revolution to deliver the desired increment of medication, then the motor can be controlled to stop when 360 encoder counts are received.

The encoder sensor 406 transmits the encoder pulses to an encoder logic circuit 407 which in turn communicates the counts to a processing unit, such as microcontroller 408. A motor drive circuit 409 receives commands from the microcontroller 408 and when so instructed, causes electrical power to be transmitted to the motor 404. A motor drive sensor circuit 410 measures the motor operating parameters such as motor voltage, motor current, and motor operating time, and transmits these parameters to the microcontroller 408. A battery 411 provides power for all of these components. The microcontroller 408 receives its operating instructions from software stored in random access memory (RAM), read only memory (ROM), or other devices known in the art for storing operating instructions for use by the microcontroller.

It will be appreciated that the foregoing computing environment is illustrative only. Any alternative computing environment involving a computer, a microcontroller or a microprocessor along with computer instruction code and circuitry is acceptable. For example, the microporcessor control may include RAM or ROM programs. Moreover, this can further be accomplished with a hardwired or programmable logic array driven state machine. Alternatively, a dedicated logic or a programmable logic array can be used to perform the operations necessary to test for an occlusion.

Figure 2:
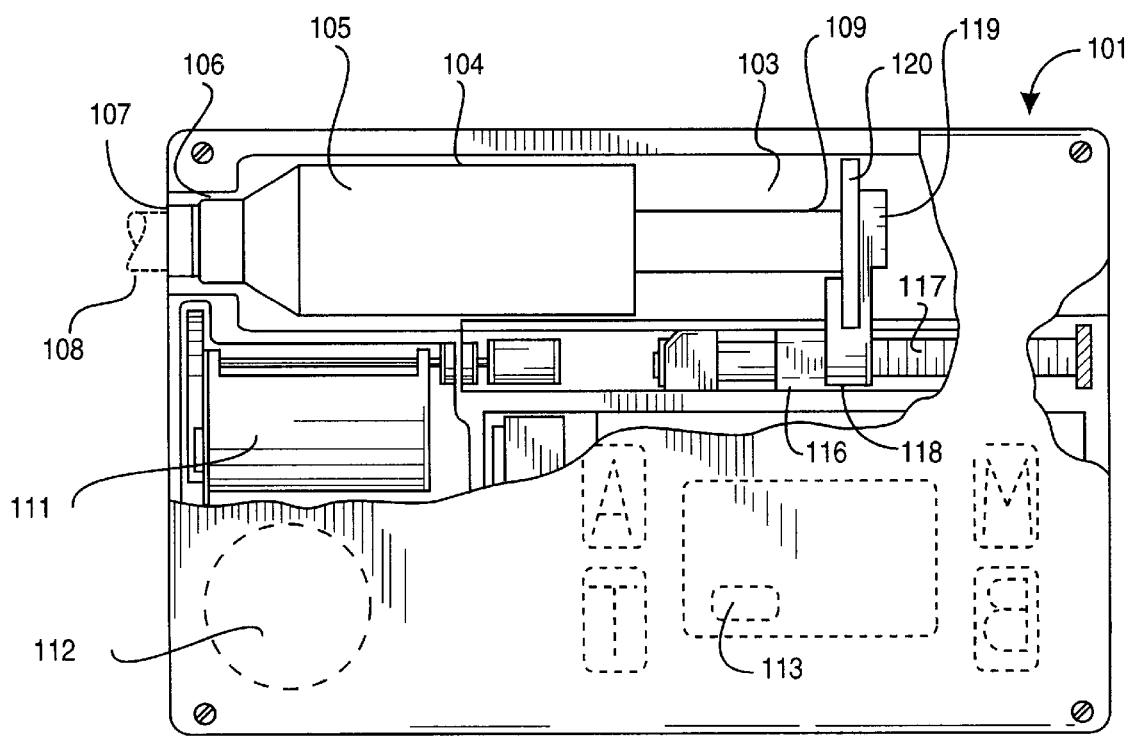
FIG. 2 is an enlarged, side plan, partial cut-away view of the infusion pump of FIG. 1 with portions broken away to illustrate certain pump components.

The improved occlusion detector described herein can be applied to the pump drive designs of FIGS. 1–3, or any other design incorporating a motor. The pumping mechanism can use DC motors, AC motors, stepper motors, solenoid motors, lead screws, cams, ratchets, jacks, piezoelectric caterpillar drives, Nitinol effectors, electrochemical gas cells or thermally driven gas or bimetallic actuators. The occlusion detector measures increased reservoir pressure indirectly by monitoring one or more motor parameters, such as voltage, current, running time, or rotational or linear displacement.

It is known in the art that torque developed by a brushed DC motor is directly proportional to the current supplied to it at steady state. Therefore, in a screw type drive system, as the axial load increases due to increased fluid pressure within the reservoir, more motor torque is required to drive the system.

Should there be an occlusion, the pressure inside the reservoir will exceed a predetermined threshold. Thus the current necessary to drive that load will exceed a predetermined current threshold and the electronics will be flagged to cease further delivering. In addition, an audible, tactile and/or display alarm typically is triggered.

However, care must be employed when clearing this alarm if the occlusion still exists and there is still a high pressure state in the reservoir. Since the motor must operate to obtain an indication of pressure within the reservoir, more and more pressure can potentially be developed within the system. If the motor is not in operation, there is no current flowing and negligible torque on the motor body. Therefore, when an occlusion exits distal from the reservoir due to pinched tubing for example, then the measured property will indicate this only during each motor delivery increment.

If the user clears the alarm and attempts to deliver medication again when the occlusion in fact was not removed, additional pressure will be generated within the fluid system. Assuming that the system is programmed to continue to alarm when the pressure (or motor current) is above the set point, then continued alarming will occur. Thus the user may on several occasions attempt to clear the alarm before locating and correcting the source of the occlusion.

When the occlusion is finally cleared, there could be excess pressure developed in the system which could result in the delivery of a bolus of medication larger than that which should be delivered. The improved occlusion detection system disclosed herein protects against this by causing the pump to rewind by some predetermined amount following each occlusion alarm. By rewinding the pump by, say, one delivery pulse, the occlusion alarm will trigger if the occlusion still exists. However it will do so at the same maximum pressure as programmed and not at above this value.

On a drive system that is bidirectional, such as that depicted in FIG. 3, the current measurement can also be used as an indicator of system wear. Over the life of the product, it is expected that the torque required to drive the system will change over time due to wear of the dynamic components and their interfaces. Since the torque required to rewind a bidirectional system is due to the drive system's frictional factors, the current to rewind can be recorded and is proportional to this torque.

As the system wears, the torque and therefore the current to rewind will change. By storing the rewind current, this can be used to calibrate the system. An averaged baseline rewind current can be determined and used to adjust the driving force baseline which is the torque (or current) required to advance the drive system when no other external forces, such as a syringe with fluid, are present. An alternative method would be to rewind the system, and then immediately thereafter, obtain the forward or driving baseline current by driving the system forward for some distance and recording it, after which, the system is rewound again. The advantage of using either method is that the calibration can be automatic and transparent to the user.

Figure 5:
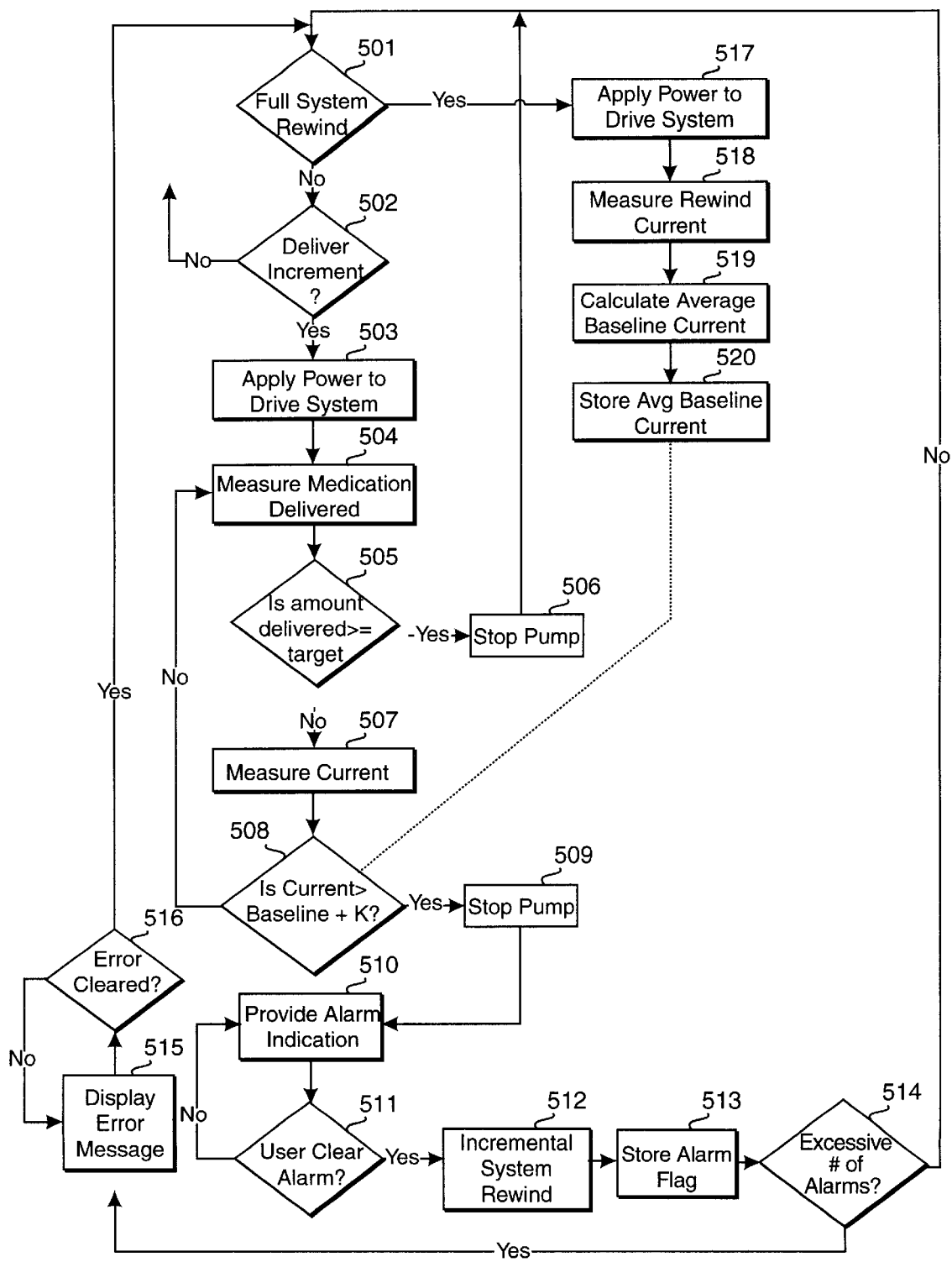
FIGS. 5–7 illustrate different embodiments of logic for detecting occlusions in accordance with certain embodiments of the present invention.

FIG. 5 illustrates the logic in one embodiment of the detector wherein motor current is measured for detecting a system occlusion. Control begins at block 501 where the system determines whether it is necessary to fully rewind the pump drive system. Conditions requiring such a rewind of the drive system will be discussed below. If the system is not to be rewound, then a determination is made whether it is time for an increment of medication is to be delivered (block 502). This determination is a function of the programming which is unique to the medical condition of each user, the type of medication being provided, or the like. If it is not time to deliver medication, then the program loops to the start for additional time to elapse or for the receipt of other control commands.

However, if it is time for delivery of an increment of medication, control transfers to block 503 where power is applied to the pump motor thus causing medication to be dispensed from the reservoir. Next, the amount of medication delivered from the reservoir is measured (block 504). This can be accomplished directly or indirectly in several ways, including measuring (1) encoder counts, (2) pump operation time, (3) reservoir plunger position location, velocity or acceleration, (4) the location of any moveable component on the pump drive train, or (5) the mass or volumetric flow of the liquid.

A determination is then made as to whether the amount of medication delivered is sufficient (block 505). If it is sufficient, control is transferred to block 506 where the pump is stopped and the program loops to the beginning. If on the other hand, the pump is continuing to run, but the programmed dosage has not yet been delivered, then the pump motor current is measured (block 507). If there is an occlusion in the system, an increase in reservoir fluid pressure will likely result. This, in turn, can cause greater motor torque and current as the motor attempts to advance the reservoir plunger against this fluid pressure. Thus, if the measured motor current is some amount greater than a known, average baseline motor current, which may be established when there was no occlusion condition, then it is determined that an occlusion condition has likely occurred.

Not only can this current measurement indicate an occlusion condition, this motor current can provide feedback as to drive system characteristics, performance, and functionality, especially with the addition of an encoder. If for example, there was a failure of the gearbox causing the motor to be unable to rotate, the measured current would be high (above predetermined threshold settings) and the encoder would not increment. This would be an indication of a drive system fault. For the inline drive system shown in FIG. 3, a failure of the gearbox, screw, or slide interface would be indicated by this condition.

Referring to FIG. 5, at block 508 the value of the average baseline current is retrieved from a storage location in memory represented by block 520. This value is compared with the current measured at the present time and a determination is made whether the present current exceeds the average baseline by a certain amount. If it does not, then the pump continues to run and control loops to block 504 where the amount of medication delivery is again measured. On the other hand, if the present current exceeds the average baseline by a selected amount, then the pump motor is stopped and an alarm indication, audible, tactile and/or visible, is given (blocks 509 and 510).

Control transfers to block 511 where the system is monitored for clearing of the alarm. If the alarm has not been cleared, then control loops to block 510 where the alarm will continue to display. If the alarm has been cleared by the user, then control transfers to block 512 where the drive system is rewound by an incremental amount. This rewinding serves to decrease the reservoir fluid back pressure which in turn inhibits or prevents the delivery of an excessive bolus of medication should the user experience a series of occlusion alarms before successfully clearing the occlusion.

Control then transfers to block 513 where an alarm flag is stored. A determination is made whether there have been an excessive number of recent alarms (block 514). If there have not, then control loops to the beginning (block 501) where the above described process is repeated. On the other hand, if there have been an excessive number of recent alarms, control transfers to block 515 where an error or reset message is displayed to the user. This message typically would be used to advise the user to contact the manufacturer or some authorized repair facility to determine the cause of the excessive number of alarms. This error message will continue to be displayed until the error is cleared (block 516) at which point control loops to the beginning (block 501) where the process is repeated.

Returning to block 501, there are times when a full rewind of the drive system may be required. One instance would be when the medication reservoir in the pump housing is empty and a new reservoir must be inserted. Thus, when it has been determined that rewinding of the drive system is desired (either by user command or otherwise), control transfers to block 517 where power is applied to the pump motor. As the motor is running in a rewind direction, the pump motor current is measured (block 518). An alternative method would be to obtain the forward or driving baseline current by driving the system forward (possibly immediately following rewind) for some distance and recording it, after which the system may need to be rewound again. Because the motor is running in the opposite direction (or forward following rewind), typically there is little or no fluid pressure against which the pump motor is driving. Thus the current measured during this phase can be used as a baseline for comparison in detecting occlusions.

Control transfers to block 519 where the previous average baseline current value is retrieved from a storage location in memory (block 520) and an updated average baseline current is calculated. This updated value is then placed in the storage location, (block 520), where it will be available for the next current measurement and comparison at block 508.

The value of repeatedly updating the average baseline current is to provide a calibration against changing drive train friction forces. The lead screw mechanism of many pump designs includes seals, a drive nut, a lead screw/motor coupling, and a bearing. All of these components have frictional properties. These properties are known to change over time and thus the motor torque and current required to advance a reservoir plunger are likely to change. This therefore provides a more accurate baseline against which current can be measured for the detection of an occlusion.

Although the foregoing description involved the measurement of motor current, other motor parameters which vary with differing fluid back pressures can be measured with like effect. Such parameters may include motor voltage, linear displacement, rotary displacement, torque, rotor speed, and the like.

For example, one alternative embodiment of the occlusion detector involves the use of a motor position encoder which can detect the motor's linear or rotational displacement. If for example, the encoder has a resolution of 360 counts per motor revolution of a rotary motor, then with each motor revolution, the sensor will provide 360 encoder signal pulses. If the pump system were designed to require one complete motor revolution to deliver the desired increment of medication, then the motor can be controlled to stop when 360 encoder counts are received. Linear displacements of linear motors may be similarly detected by suitable linear encoders or sensors.

Because motors have inertia, the power supplied to them must be removed prior to the actual stopping position in order for the motor to slow and stop. The slowing or deceleration can be accomplished in several ways including: (1) coasting which simply lets the applied and frictional torque slow the motor; or (2) dynamic braking which can be accomplished for example by shorting the motor leads or applying a potential in the opposite direction.

The applied torque affects the total rotational count. Thus as the applied torque varies, so will the error from the desired 360 counts. To account for a deviation from the target encoder count, a feedback loop is provided whereby the input power parameters to the motor, such as motor voltage or current or the time during which power is applied to the motor, may be adjusted.

In one embodiment, the motor is controlled based on the results of the previous encoder count for each cycle. Thus, for example, if 360 encoder counts were desired, but only 350 were measured, then subsequent input motor parameters can be adjusted such that the running encoder average is maintained at 360 counts. If a motor system was used with a DC motor driven with a constant current source or fixed source voltage, then the motor input parameter to be adjusted for maintaining the desired encoder count for the next pump cycle would be power on time.

For example, a motor may be driven such that half of the rotational displacement (or 180 out of 360 counts) is due to power on time and the other half is due to the coasting down of the motor under a specified nominal load (torque). Should the load increase, then the coasting would decrease thereby reducing the total encoder count measured for a constant power input. For example, the system may measure 350 counts rather than the target value of 360 counts. To maintain medication delivery accuracy therefore, the subsequent motor increment during the next pump cycle may be increased above the 180 encoder count for the power on time so that the running average is maintained at 360 for the entire pump cycle.

Figure 6:
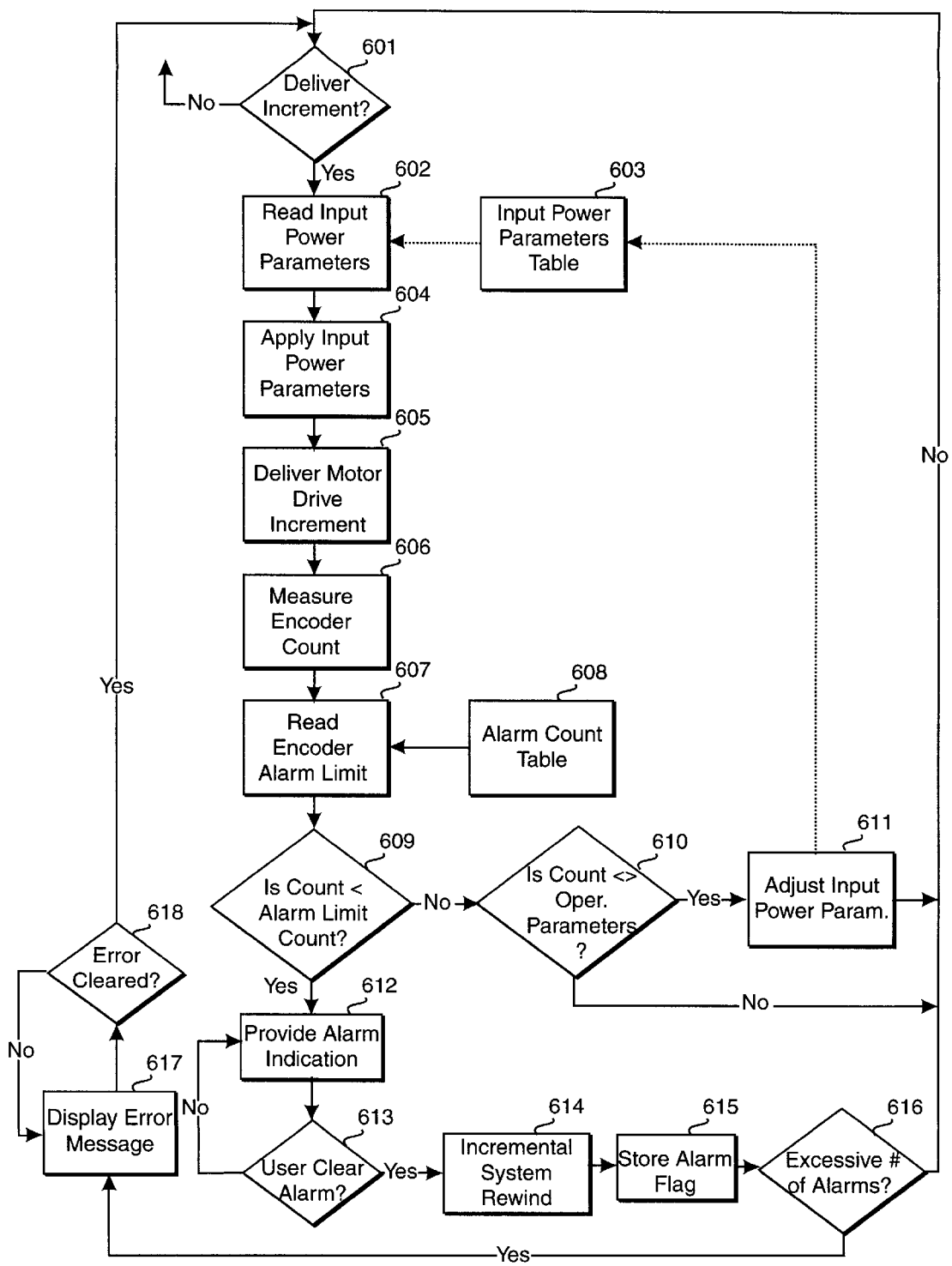

FIG. 6 illustrates an example of the logic of an embodiment of the present invention using an encoder. Control begins at block 601, where a determination is made whether it is time for an increment of medication is to be delivered. The same considerations apply here as was described for block 502 of FIG. 5. If it is not time to deliver medication, then the program loops to the start in order for additional time to elapse or for the receipt of other control commands.

However, if it is time for delivery of an increment of medication, control transfers to block 602 where the applicable input power parameters are read from a memory storage location represented by block 603. Such power parameters would include pump power on time, operating voltage and operating current. These parameters are applied to the pump to drive it for one pump cycle. This causes an increment of medication to be delivered as the pump runs for a discrete period of time (blocks 604 & 605). The pump encoder counts are measured during this motor drive increment (block 606). Counts are measured both during the time that power is applied to the pump motor as well as the time during which the pump coasts down.

Control transfers to block 607 where the encoder count occlusion alarm limit number is read from the storage location represented by block 608. This alarm limit number is compared with the encoder count just measured (block 609). If the encoder count is smaller than the alarm limit amount, then it is determined that the pump motor may have experienced excessive torque which can be associated with an occlusion or a drive system problem. If this occurs, then control transfers to block 612 where an alarm (audible, tactile and/or visual) is rendered. The alarm process represented by blocks 612 through 618 (including the incremental drive system rewind) is the same as previously described for blocks 510 through 516 of FIG. 5.

Although not shown in FIG. 6, it can be appreciated that the alarm count table (block 608) can be calibrated to adjust for changes in system friction properties over time in a manner similar to that which was described in FIG. 5, blocks 517–520. In the embodiment of FIG. 6, the pump drive system periodically could be rewound thereby removing any system fluid pressure forces from the pump drive system. Then input power parameters could be applied to the pump in either a forward or reverse direction to generate one pump cycle. The encoder count could be measured during this pump cycle and used to calculate a baseline average encoder alarm count for storage in the alarm count table (block 608).

Returning to block 609 of FIG. 6, if the encoder count is not less than the alarm limit, then control transfers to block 610 where a determination is made whether the encoder count is outside of an operating parameter range for purposes of adjusting the input power parameters. For example, if the encoder count should be 360 counts for the proper medication delivery increment, but during the current cycle, only 350 counts were measured, then this might not be low enough to indicate an occlusion condition. However a 350 count might indicate a need for an input power adjustment for the next increment delivery cycle. One possible adjustment might comprise an increase in the pump power on time.

If it is determined that an input power parameter adjustment is needed, control is transferred to block 611 where the adjustment amount is calculated and stored in the memory location represented by block 603. Control then loops to block 601 where the above described process is repeated. On the other hand if the increment count is such that no adjustment is needed, then control loops directly to block 601. Thus, the process represented by blocks 610, 611 and 603 constitutes a feedback loop for maintaining the average encoder count at the same level.

Yet another embodiment of the occlusion detector uses an encoder count to determine torque. In this embodiment, torque is a function of encoder count and one or more motor input power parameters. Motor load torque can be determined by evaluating the stored encoder count for a known delivered amount of energy. The detector system provides a known amount of energy (i.e., power times motor on-time), and records the motor displacement via the number of encoder counts obtained. Using a look-up table or calculated value, the system determines a corresponding torque that would result from the recorded number of encoder pulses for the amount of energy supplied.

For example, if the motor were running for a certain amount of time, this might result in an encoder count of 360. Later, the motor might run for the same amount of time under the same voltage and current conditions, but an encoder count of 350 may result. Thus the system would have encountered increased torque as reflected by the reduced encoder count. A lookup table or calculated value of torque vs encoder count and input power parameters can thereby be developed and used to measure motor torque.

Figure 7:
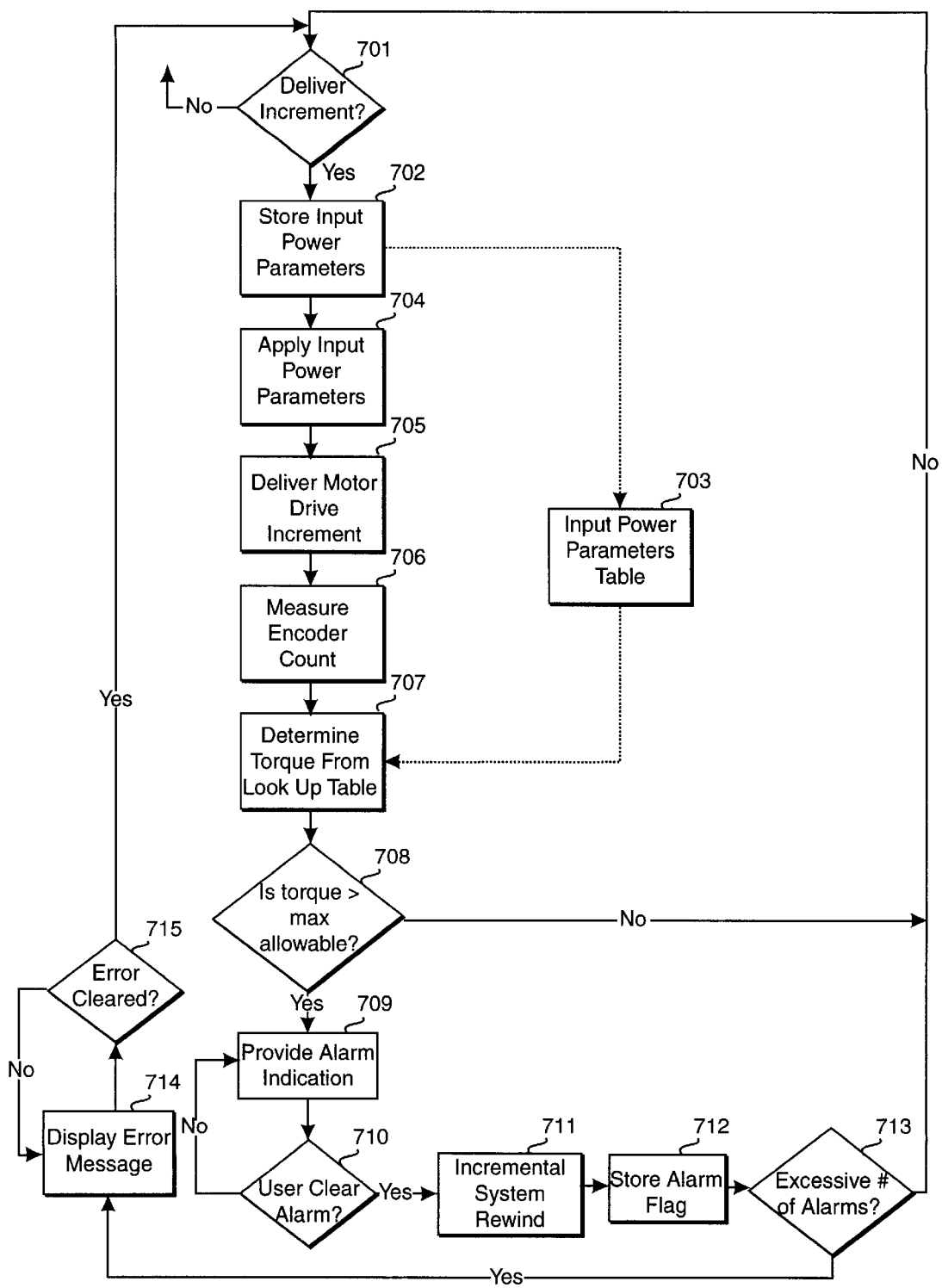

FIG. 7 illustrates an example of the logic of an embodiment of the present invention which uses an encoder to measure torque. Control begins at block 701 where a determination is made whether it is time to deliver a medication dosage increment. If it is time to deliver a dose, then control transfers to block 702 where the pump input power parameters which will be used on the upcoming cycle are stored in a storage location of an input power look up table represented by block 703. Next, these same input power parameters are applied to the pump motor which operates for the selected time interval and delivers the dosage increment (blocks 704 & 705). The encoder count is measured for this cycle, including counts measured both during the pump power on time as well as the coast down of the pump motor (block 706).

Control is transferred to block 707 where the encoder count is applied to the input power parameter look up table of block 703, and the torque corresponding to the measured encoder count is determined by retrieving the torque value from the table. Alternatively, the torque can be determined by calculating it as a function of encoder count and input power parameters. Next, a determination is made whether the torque just measured exceeds the amount of torque which would correspond to an occlusion or other drive system problem (block 708). If it does not, then control loops to block 701 where the above described process is repeated.

On the other hand, if the calculated torque does exceed the amount of torque associated with an occlusion or drive system problem, control transfers to block 709 where an audible, tactile and/or visual alarm is given. The alarm process represented by blocks 709 through 715 (including incremental drive system rewind) is the same as previously described for blocks 510 through 516 of FIG. 5.

Although not shown in FIG. 7, it can be appreciated that the maximum allowable torque value used in block 708 can be calibrated to adjust for changes in system friction properties over time in a manner similar to that which was described in FIG. 5, blocks 517–520. In the embodiment of FIG. 7, the pump drive system periodically could be rewound thereby removing any system fluid pressure forces from the pump drive system. Then input power parameters could be applied to the pump in either a forward or reverse direction to generate one pump cycle. The encoder count could be measured during this pump cycle and used to calculate a baseline average torque value which in turn could be used to calculate the maximum allowable torque for use in block 708 to determine whether there is an occlusion.

In further can be appreciated that although the embodiments of FIGS. 5 through 7 were discussed separately, it may be advantageous to use more than one of these embodiments in one pump system. Doing so may provide enhanced system redundancy and safety.

In summary, preferred embodiments disclose a method and apparatus for automatically detecting an occlusion or drive system failure in a medication infusion pump system. The electrical current to an infusion pump is measured and compared against a baseline average current. If the current exceeds a threshold amount, an alarm is triggered. Alternatively, pump motor encoder pulses are measured during a pump cycle. If the number of pulses do not correspond to a normal range, an alarm is triggered. Alternatively, a system torque value is determined from the measurement of pump motor encoder pulses during a pump cycle. If the system torque value exceeds a maximum threshold value, an alarm is triggered. After any alarm is triggered, the pump motor is driven in reverse for an incremental distance in order to relieve the fluid pressure in the system.

While the description above refers to particular embodiments of the present inventions, it will be understood that many modifications may be made without departing from the spirit thereof. The accompanying claims are intended to cover such modifications as would fall within the true scope and spirit of the present inventions. The presently disclosed embodiments are therefore to be considered in all respects as illustrative and not restrictive, the scope of the inventions being indicated by the appended claims rather than the foregoing description, and all changes which come within the meaning and range of equivalency of the claims are therefore intended to be embraced therein.

What is claimed is:

1. A method of detecting an occlusion in a fluid pump system, comprising:
    applying input power parameters to a pump motor to provide a first pump cycle;
    measuring a first encoder count during the first pump cycle;
    determining whether the first encoder count is less than a first value; and
    rewinding the fluid pump system at least to the point of reducing pressure in the fluid pump system after determining that the first encoder count is less than the first value.

2. The method of claim 1 further comprising providing an alarm indication after determining that the first encoder count is less than the first value.

3. The method of claim 1 further comprising:
    determining whether the first encoder count is equal to a third value; and
    adjusting the input power parameters to provide a second pump cycle after determining that the first encoder count does not equal the third value, said second pump cycle resulting in a second encoder count, said second encoder count being one of a value greater than the first encoder count if the first encoder count is less than the third value and a value smaller than the first encoder count if the first encoder count is greater than the third value.

4. A method of detecting an occlusion in a fluid pump system, comprising:
    applying input power parameters to a pump motor to provide a first pump cycle;
    measuring a first encoder count during the first pump cycle;
    determining whether the first encoder count is less than a first value;
    providing an alarm indication after determining that the first encoder count is less than the first value;
    calculating a total number of alarm indications after determining that the first encoder count is less than the first value;
    determining whether the total number of alarm indications exceeds a second value; and
    providing a system error message after determining that the total number of alarm indications exceeds the second value.

5. A method of detecting an occlusion in a fluid pump system, comprising:
    applying input power parameters to a pump motor to provide a first pump cycle;
    measuring a first encoder count during the first pump cycle;
    determining whether the first encoder count is less than a first value;
    rewinding the fluid pump system at least to the point of reducing pressure in the fluid pump system after determining that the first encoder count is less than the first value;
    providing an alarm indication after determining that the first encoder count is less than the first value;
    calculating a total number of alarm indications after determining that the first encoder count is less than the first value;
    determining whether the total number of alarm indications exceeds a second value;
    providing a system error message after determining that the total number of alarm indications exceeds the second value;
    determining whether the first encoder count is equal to a third value; and
    adjusting the input power parameters to provide a second pump cycle after determining that the first encoder count does not equal the third value, said second pump cycle resulting in a second encoder count, said second encoder count being one of a value greater than the first encoder count if the first encoder count is less than the third value and a value smaller than the first encoder count if the first encoder count is greater than the third value.

6. A system for detecting an occlusion in a fluid pump system, comprising:
   a processing unit capable of communicating with the fluid pump system; and
   program logic executed by the processing unit, comprising:
   means for applying input power parameters to a pump motor to provide a first pump cycle;
   means for measuring a first encoder count during the first pump cycle;
   means for determining whether the first encoder count is less than a first value; and
   means for rewinding the fluid pump system at least to the point of reducing pressure in the fluid pump system after determining that the first encoder count is less than the first value.

7. The system of claim 6 wherein the program logic further comprises means for providing an alarm indication after determining that the first encoder count is less than the first value.

8. The system of claim 6 wherein the program logic further comprises:
   means for determining whether the first encoder count is equal to a third value; and
   means for adjusting the input power parameters to provide a second pump cycle after determining that the first encoder count does not equal the third value, said second pump cycle resulting in a second encoder count, said second encoder count being one of a value greater than the first encoder count if the first encoder count is less than the third value and a value smaller than the first encoder count if the first encoder count is greater than the third value.

9. A system for detecting an occlusion in a fluid pump system, comprising:
   a processing unit capable of communicating with the fluid pump system; and
   program logic executed by the processing unit, comprising:
   means for applying input power parameters to a pump motor to provide a first pump cycle;
   means for measuring a first encoder count during the first pump cycle;
   means for determining whether the first encoder count is less than a first value; and
   means for providing an alarm indication after determining that the first encoder count is less than the first value;
   means for calculating a total number of alarm indications after determining that the first encoder count is less than the first value;
   means for determining whether the total number of alarm indications exceeds a second value; and
   means for providing a system error message after determining that the total number of alarm indications exceeds the second value.

10. A system for detecting an occlusion in a fluid pump system, comprising:
    a processing unit capable of communicating with the fluid pump system; and
    program logic executed by the processing unit, comprising:
    means for applying input power parameters to a pump motor to provide a first pump cycle;
    means for measuring a first encoder count during the first pump cycle;
    means for determining whether the first encoder count is less than a first value;
    means for rewinding the fluid pump system at least to the point of reducing pressure in the fluid pump system after determining that the first encoder count is less than the first value;
    means for providing an alarm indication after determining that the first encoder count is less than the first value;
    means for calculating a total number of alarm indications after determining that the first encoder count is less than the first value;
    means for determining whether the total number of alarm indications exceeds a second value;
    means for providing a system error message after determining that the total number of alarm indications exceeds the second value;
    means for determining whether the first encoder count is equal to a third value; and
    means for adjusting the input power parameters to provide a second pump cycle after determining that the first encoder count does not equal the third value, said second pump cycle resulting in a second encoder count, said second encoder count being one of a value greater than the first encoder count if the first encoder count is less than the third value and a value smaller than the first encoder count if the first encoder count is greater than the third value.

11. A method of operating a fluid pump system, comprising:
    applying a power parameter to deliver a motor drive increment to the fluid pump system;
    measuring a response of the fluid pump system to the power parameter so applied;
    determining if the power parameter and the response of the fluid pump system are within a predetermined acceptable limit; and
    rewinding the fluid pump system at least to the point of reducing pressure in the fluid pump system if the power parameter and the response of the fluid pump system are not within the predetermined acceptable limit.

12. The method of claim 11, wherein the step of measuring a response of the fluid pump system to the power parameter includes reading encoder counts.

13. The method of claim 11, wherein the power parameter is an amount of power and the step of determining comprises determining if the amount of power used to deliver a motor drive increment to the fluid pump system is about equal to an expected amount of power to be used to deliver a motor drive increment to the fluid pump system.

14. The method of claim 11, further including adjusting the power parameter to deliver a motor drive increment to the fluid pump system if the power parameter and the response of the fluid pump system are not within the predetermined acceptable limit.

15. The method of claim 11, further including providing an alarm if the power parameter and the response of the fluid pump system are not within the predetermined acceptable limit.

16. The method of claim 11, wherein the step of applying the power parameter to drive the motor includes reading one or more input power parameters from a memory.

17. The method of claim 16, further including modifying the one or more input power parameters in the memory if the power parameter and the response of the fluid pump system are not within the predetermined acceptable limit.

* * * * *